(12) United States Patent
Franklin et al.

(10) Patent No.: US 10,098,821 B2
(45) Date of Patent: Oct. 16, 2018

(54) PROCESS OF MANUFACTURE OF AN ANTIPERSPIRANT COMPOSITION

(71) Applicant: Conopco, Inc., Englewood Cliffs, NJ (US)

(72) Inventors: Kevin Ronald Franklin, Wirral (GB); Anestis Kastrinakis, Leeds (GB); Craig James Luckwell, Leeds (GB); Philip Christopher Waterfield, Heswall (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/525,455

(22) PCT Filed: Nov. 11, 2015

(86) PCT No.: PCT/EP2015/076365
§ 371 (c)(1),
(2) Date: May 9, 2017

(87) PCT Pub. No.: WO2016/078991
PCT Pub. Date: May 26, 2016

(65) Prior Publication Data
US 2017/0333307 A1 Nov. 23, 2017

(30) Foreign Application Priority Data
Nov. 19, 2014 (EP) .................................. 14193902

(51) Int. Cl.
*A61K 8/26* (2006.01)
*A61K 8/20* (2006.01)
*A61K 8/34* (2006.01)
*A61K 8/44* (2006.01)
*A61K 8/06* (2006.01)
*A61Q 15/00* (2006.01)

(52) U.S. Cl.
CPC ................ *A61K 8/26* (2013.01); *A61K 8/062* (2013.01); *A61K 8/20* (2013.01); *A61K 8/34* (2013.01); *A61K 8/44* (2013.01); *A61Q 15/00* (2013.01)

(58) Field of Classification Search
None
See application file for complete search history.

(56) References Cited

U.S. PATENT DOCUMENTS

| | | | |
|---|---|---|---|
| 3,792,068 | A | 2/1974 | Luedders et al. |
| 4,183,911 | A | 1/1980 | Smithies et al. |
| 4,359,456 | A | 11/1982 | Gosling et al. |
| 4,435,382 | A | 3/1984 | Shin et al. |
| 5,744,130 | A | 4/1998 | Guskey et al. |
| 5,955,065 | A | 9/1999 | Thong et al. |
| 6,042,816 | A | 3/2000 | Shen |
| 6,261,543 | B1 | 7/2001 | Fletcher et al. |
| 6,511,243 | B2 | 1/2003 | Miranda |
| 6,911,195 | B2 | 6/2005 | Vu |
| 6,942,850 | B2 | 9/2005 | Coe |
| 7,087,220 | B2 | 8/2006 | Li |
| 7,704,531 | B2 | 4/2010 | Tang et al. |
| 2003/0049219 | A1 | 3/2003 | Lemoine et al. |
| 2003/0215399 | A1 | 11/2003 | Smith et al. |
| 2004/0115147 | A1 | 6/2004 | Vu et al. |
| 2005/0163737 | A1 | 7/2005 | Lemoine et al. |
| 2006/0204463 | A1 | 9/2006 | Tang et al. |
| 2006/0222612 | A1 | 10/2006 | Ni et al. |
| 2007/0020211 | A1 | 1/2007 | Li et al. |
| 2007/0196303 | A1 | 8/2007 | Li et al. |
| 2007/0286830 | A1 | 12/2007 | Li et al. |
| 2008/0131354 | A1 | 6/2008 | Li |
| 2008/0241089 | A1 | 10/2008 | Banowski et al. |
| 2008/0267895 | A1 | 10/2008 | Franklin et al. |
| 2010/0303749 | A1 | 12/2010 | Pan |
| 2011/0038823 | A1* | 2/2011 | Phipps ..................... A61K 8/06 424/68 |
| 2011/0038902 | A1 | 2/2011 | Phipps et al. |
| 2011/0274637 | A1 | 11/2011 | Milardovic et al. |
| 2014/0178321 | A1 | 6/2014 | Banowski et al. |
| 2014/0301963 | A1 | 10/2014 | Claas et al. |

FOREIGN PATENT DOCUMENTS

| | | |
|---|---|---|
| CN | 1323191 | 11/2001 |
| EP | 0308937 | 3/1989 |
| EP | 0405598 | 1/1991 |
| EP | 1175165 | 4/2000 |
| EP | 1104282 | 6/2001 |
| GB | 2113116 | 8/1983 |
| WO | WO0010512 | 3/2000 |
| WO | WO2008063188 | 5/2008 |
| WO | WO2009044381 | 4/2009 |
| WO | WO2009075678 | 6/2009 |
| WO | WO2009076592 | 6/2009 |
| WO | WO2011016807 | 2/2011 |
| WO | WO2012021356 | 2/2012 |
| WO | WO2012060817 | 5/2012 |
| WO | WO2012061280 | 5/2012 |
| WO | WO2012148480 | 11/2012 |
| WO | WO2013158077 | 10/2013 |
| WO | WO2012148481 | 11/2014 |
| WO | WO2014187684 | 11/2014 |
| WO | WO2014187685 | 11/2014 |

OTHER PUBLICATIONS

Pluronic(R) F-127, Newdruginfo.com, Jun. 7, 2016, 1 page.
(Continued)

*Primary Examiner* — Robert A Wax
*Assistant Examiner* — Melissa S Mercier
(74) *Attorney, Agent, or Firm* — Karen E. Klumas

(57) ABSTRACT

A process for manufacture of an antiperspirant composition comprising the reaction of an aqueous solution of aluminum sesquichlorohydrate, water soluble calcium salt and amino acid, at a total anhydrous solids content of from 33 to 60% by weight and at a temperature of at least 65° C., for a period of from 1 to 24 hours, wherein the molar ratio of water soluble calcium salt to aluminum sesquichlorohydrate is at least 1:40 and the molar ratio of amino acid to aluminum sesquichlorohydrate is at least 1:20, the mixture then being cooled to less than 25° C. and diluted with at least an equal weight of water or to a total anhydrous solids content of less than 31% by weight, the dilution phase being performed within 10 days of cooling phase.

17 Claims, No Drawings

(56) References Cited

OTHER PUBLICATIONS

Laden, Antiperspirants and Deodorants 1999 2nd Edition pp. 96-97, Antiperspirants and Deodorants 1999 2nd edition pp. 96-97, 1999, pp. 96-97, 2nd Edition.
IPRP2 in PCTEP2014059583, Sep. 11, 2015.
IPRP2 in PCTEP2014060306, Sep. 16, 2015.
IRPR2 in PCTEP2015074529, Dec. 2, 2016.
Search Report & Written Opinion in PCTEP2015074528, dated Jan. 20, 2016.
Search Report & Written Opinion in PCTEP2015074529, dated Dec. 21, 2015.
Search Report & Written Opinion in PCTEP2015076365, dated Feb. 11, 2016.
Search Report & Written Opinion in PCTEP2016080034, dated Feb, 9, 2017.
Search Report in EP13168417, dated Oct. 31, 2013 .
Search Report in EP13168418, dated Oct. 31, 2013.
Search Report in EP14190530, dated Feb. 12, 2015.
Search Report in EP14190531, dated May 8, 2015.
Search Report in EP14193902, dated May 6, 2015.
Search Report in PCTEP2014059582, dated Oct. 6, 2014.
Search Report in PCTEP2014059583, dated Oct. 6, 2014.
Search Report in PCTEP2014060306, dated Oct. 6, 2014.
Written Opinion 1 in PCTEP2014059583, dated Oct. 6, 2014.
Written Opinion 2 in PCTEP2014059583, dated Apr. 30, 2015.
Written Opinion 2 in PCTEP2014060306, May 8, 2015.
Written Opinion in EP13168417, dated Oct. 31, 2013.
Written Opinion in EP13168418, dated Oct. 31, 2013.
Written Opinion in EP14190530, dated Feb. 12, 2015.
Written Opinion in EP14190531, dated May 8, 2015.
Written Opinion in EP14193902, dated May 6, 2015.
Written Opinion in PCTEP2014059582, dated Oct. 6, 2014.
Written Opinion 1 in PCTEP2014060306, dated Oct. 6, 2014.
Written Opinion in PCTEP2015074529, dated Sep. 6, 2016.
IRPR2 in PCTEP2015074528, Jan. 18, 2016.
Co-pending U.S. Appl. No. 14/889,866, Karim Mohamed Anwar M Fawz, filed Nov. 9, 2015.
Co-pending U.S. Appl. No. 14/889,863, Karim Mohamed Anwar M Fawz, filed Nov. 9, 2015.
Co-pending U.S. Appl. No. 14/547,501, Kevin Ronald Franklin, filed Nov. 19, 2014.
Search Report and Written Opinion in EP17199987, dated Dec. 6, 2017.
IPRP in PCTEP2016080034, Feb. 14, 2018.
Karl Laden, Chemistry of Aluminum-Zirconium-Glycine (AZG) Complexes, Antiperspirants and Deodorants, 1999, pp. cover pages, title pages & p. 137 (total of 4 pages), vol. 20, Second Edition.

* cited by examiner

PROCESS OF MANUFACTURE OF AN ANTIPERSPIRANT COMPOSITION

The present invention is concerned with methods of making antiperspirant compositions. It is particularly concerned with the manufacture of compositions comprising activated aluminium sesquichlorohydrate (herein ASCH).

Traditionally, activated aluminium chlorohydrate (herein ACH) compositions have been prepared by prolonged heating of ACH solutions followed by spray drying; see, for example, U.S. Pat. No. 4,359,456 (Gosling). The samples prepared by this method needed to be formulated into essentially anhydrous compositions in order for the antiperspirant to maintain its high activity.

Activated ACH compositions have also been prepared using water soluble calcium acids, particularly with a further adjunct such as an amino acid, hydroxyl acid, or betaine. Some of these aqueous compositions have reasonable stability, the antiperspirant not quickly losing its enhanced activity.

EP 1,104,282 (Gillette) discloses a means of producing activated ACH compositions using a water soluble calcium salt and an amino acid or a hydroxy acid.

U.S. Pat. No. 6,911,195 (Gillette) discloses water-in-oil emulsion gels comprising aluminium-zirconium antiperspirant salts activated using calcium ions.

U.S. Pat. No. 5,955,065 (Gillette) discloses anhydrous suspension formulations comprising particulate BAC and aluminium-zirconium antiperspirant salts activated using calcium ions.

U.S. Pat. No. 6,942,850 (Gillette) discloses aqueous alcoholic composition comprising aluminium-zirconium antiperspirant salts activated using calcium ions.

WO 2009/044381 (P&G) discloses water-in-oil emulsion sticks comprising ACH and aluminium-zirconium antiperspirant salts activated using calcium ions.

U.S. Pat. No. 7,704,531 (Colgate) discloses compositions comprising an active system made from combining an aluminium or aluminium-zirconium salt, a calcium salt, and a betaine.

US 2011/0038823 (Dial/Henkel) discloses water-in-oil emulsion sticks comprising an antiperspirant active prepared by combining ACH, calcium chloride and glycine.

US 2007/196303, US 2007/0020211, WO 2008/063188, US 2008/0131354 and U.S. Pat. No. 7,087,220 (Summit and Reheis) each describe methods of making calcium-activated antiperspirant salts.

It is an object of the present invention to avoid rheological instability in aqueous antiperspirant compositions and in aqueous solutions of antiperspirant salts that may be used in the manufacture of the same.

It is a further object of the present invention to provide a process for manufacture of an antiperspirant composition having good environmental process efficiency, in particular good environmental process efficiency in terms of energy and water usage.

In a first aspect of the invention, there is provided a process for manufacture of an antiperspirant composition comprising the reaction of an aqueous solution of aluminium sesquichlorohydrate, water soluble calcium salt and amino acid, at a total anhydrous solids content of from 33 to 60% by weight and at a temperature of at least 65° C., for a period of from 1 to 24 hours, wherein the molar ratio of water soluble calcium salt to aluminium is at least 1:40 and the molar ratio of amino acid to aluminium is at least 1:20, the mixture then being subjected to a cooling phase in which it is cooled to less than 25° C. and a dilution phase in which it is diluted with at least an equal weight of water or to a total anhydrous solids content of less than 31% by weight, the dilution phase being performed within 10 days of cooling phase.

In a second aspect of the present invention, there is provided an antiperspirant composition prepared according to the first aspect of the invention.

In a third aspect of the present invention there is provided a cosmetic method of attaining an antiperspirancy benefit comprising the topical application of a composition according to the second aspect of the present invention to the surface of the human body.

The present invention involves the activation of aluminium sesquichlorohydrate with a water soluble calcium salt, typical calcium chloride, and an amino acid, typically glycine. This activation step is performed at elevated temperature and at relatively high total solids content, these factors helping environmental process efficiency in terms of energy and water usage. This stage of the process of manufacture is herein termed the "activation process".

Following the heat activation of the ASCH with the water soluble calcium salt and amino acid, it is crucial that the mixture is cooled and diluted relatively quickly in order to avoid catastrophic rheological problems. The present inventors have found that unless this is done, the mixture starts to gel relatively quickly and that such gelation is typically irreversible. This can lead to an unusable product which is highly undesirable.

Whilst the dilution step must be done with a certain period of the cooling step, it should be noted that dilution step may be done before the cooling step in certain embodiments, especially when the dilution is done with water at elevated temperature (vide infra).

The choice of antiperspirant salt used is critical to the success of the present invention. We have found that surprisingly good results are found on using salts commonly referred to as aluminium sesquichlorohydrate having the chemical formula $Al_2(OH)_{4.4}Cl_{1.6}$ to $Al_2(OH)_{4.9}Cl_{1.1}$. Most commercial ASCH samples are of chemical formula $Al_2(OH)_{4.7}Cl_{1.3}$ to $Al_2(OH)_{4.9}Cl_{1.1}$ and it is preferred to use salts of this formula.

The surprisingly good results referred to in the above paragraph include surprisingly good antiperspirancy performance. In addition, compositions prepared according to the present invention have remarkable storage stability, in particular rheological stability, maintaining their good performance for many months.

The ASCH salt used in the present invention has aluminium to chloride molar ratio of from 1.25:1 to 1.82:1 and preferably 1.54:1 to 1.82:1.

In order for the antiperspirant to become activated, it is important to have sufficient calcium present relative to the amount of aluminium present. The molar ratio of calcium to aluminium is at least 1:40, preferably at least 1:30 and more preferably at least 1:20. It is not advantageous to have the calcium concentration in excess of the aluminium concentration, indeed it is preferred that the calcium concentration is no more than half that of the aluminium concentration and more preferred that it is no more than a fifth of said concentration. For the preferred molar ratios of calcium to aluminium of at least 1:40 and at least 1:20, it is independently preferred that this ratio is no greater than 1:2 and more preferred that it is no greater than 1:5.

In particularly preferred embodiments, the molar ratio of calcium to aluminium is at least 1:15 and preferably no greater than 1:5 and in especially preferred embodiments it is at least 1:10 and preferably no greater than 1:5.

A preferred water soluble calcium salt for use in the present invention is calcium chloride.

Herein, references to molar amounts and ratios of "aluminium" are calculated on the basis of mono-nuclear aluminium, but include aluminium present in poly-nuclear species; indeed, most of the aluminium in the salts of relevance is present in poly-nuclear species.

In order for the antiperspirant to become activated, it is important to have sufficient amino acid present relative to the amount of aluminium present. The molar ratio of amino acid to aluminium is at least 1:20, more preferably at least 1:10 and most preferably at least 1:5. It is not advantageous to have the amino acid concentration in excess of the aluminium concentration; hence, the molar amino acid to aluminium is preferably from 1:20 to 1:1, more preferably from 1:10 to 1:1 and most preferably from 1:5 to 1:1.

In particularly preferred embodiments, the molar ratio of amino acid to aluminium is at least 1:4 and preferably no greater than 1:1 and in especially preferred embodiments it is at least 1:3 and preferably no greater than 1:1.

The presence of both calcium and amino acid is essential for the success of the present invention. In preferred embodiments, the molar ratio of calcium to aluminium is at least 1:20 and the molar ratio of amino acid to aluminium is at least 1:10. In further preferred embodiments the molar ratio of calcium to aluminium is from 1:20 to 1:5 and the molar ratio of amino acid to aluminium is from 1:10 to 1:1.

In certain especially preferred embodiments, the molar ratio of calcium to aluminium is from 1:15 to 1:5 and the molar ratio of amino acid to aluminium is from 1:4 to 1:1. In these especially preferred embodiments, exemplary performance in is obtained when the molar ratio of calcium to aluminium is from 1:10 to 1:5 and the molar ratio of amino acid to aluminium is from 1:3 to 1:1.

The above indicated preferences for calcium to aluminium molar ratio and/or amino acid to aluminium molar ratio lead to compositions of higher Band III content (vide infra) and, in general, higher antiperspirancy performance. It will be noted that higher Band III content is generally indicative of higher antiperspirancy performance.

It is noteworthy that an amino acid must be used in order to activate the antiperspirant salt. The combination of a water soluble calcium salt and a hydroxy acid, as disclosed in EP 1,104,282 (Gillette), was found to be unsuccessful. Preferred amino acids for use in the present invention are glycine, alanine, valine and proline. A particularly preferred amino acid for use in the present invention is glycine.

The activation process generally produces a mixture of aluminium species having a relatively high content of what is commonly termed Band III material, as determined by SEC (Size Exclusion Chromatography) analysis. The SEC technique employed is well known in the art and is described in further detail in U.S. Pat. No. 4,359,456 (Gosling). The SEC band commonly referred to as Band III is designated as "Peak 4" in EP 1,104,282 B1 by Gillette.

Herein, "Band III content" refers to the integrated area in the Band III region of the SEC chromatograph relative to the total integrated area in all of the regions corresponding to aluminium species; that is to say, Bands I, II, III, and IV.

In the activation process and method of manufacture described herein, it is preferred that the activation mixture is heated for sufficient time for the Band III content of the aluminium species to become at least 40%, more preferably at least 40% and most preferably at least 50%.

In the activation process and method of manufacture described herein, the activation mixture is heated to at least 65° C., preferably to at least 75° C., and more preferably to at least 85° C.

The present invention involves a particular high total concentration of anhydrous solids in the activation process. This is at least 33% by weight, but no greater than 60% by weight. In preferred embodiments the total concentration of anhydrous solids in the activation process is at least 35% and in particularly preferred embodiments it is at least 40%. The invention is of greatest importance when the total concentration of anhydrous solids in the activation process is at least 45%.

The present inventors have found a certain criticality in the cooling phase of the process of manufacture. The cooling stage is performed after the activation process and is preferably done at a relatively fast rate. Thus, it is preferred that the rate of cooling is at least 0.6° C. per minute, more preferably at least 0.9° C. per minute and most preferably at least 1.2° C. per minute. By cooling relatively quickly after the activation process, superior rheological stability may be obtained not only for the cooled solution immediately obtained, but also for any diluted antiperspirant compositions produced therefrom.

A further critical stage in the process of manufacture of the present invention is the dilution phase. This must be performed within 10 days of the cooling phase, preferably with 5 days of the cooling phase and more preferably within 3 days of the cooling phase.

The dilution involves the addition of water, and optionally other components, such that the total anhydrous solids are reduced to less than 31% by weight or the solution is diluted with at least an equal weight of water, thereby at least halving the total concentration of anhydrous solids.

It preferred that the total anhydrous solids are reduced to less than 28.5% by weight during the dilution phase and more preferred that they are reduced to less than 25% by weight, whether or not the solution is diluted with at least an equal weight of water.

When the activation process is performed at particularly high anhydrous solids levels, i.e. at least 40% by weight, it is preferred that the dilution is carried out within 7 days of the cooling phase.

When the activation process is performed at especially high anhydrous solids levels, i.e. at least 45% by weight, it is preferred that the dilution is carried out within 3 days of the cooling phase.

It is observed that the rheological problems that are encountered on storage of the highly concentrated solution of the activation process of the present invention are very much reduced following cooling and dilution as described herein.

Herein, the total anhydrous solids include any components that would be solid at 20° C. and 1 atmosphere, excluding any water of crystallisation or hydration with which they might usually or possibly be associated in their solid state.

Some criticality has also been found in the conditions used in the dilution phase. Thus, it is preferred that the dilution is performed whilst the activation process mixture is still at a temperature of at least 65° C. It is further preferred that this hot mixture is diluted with water that is also at elevated temperature, in particular that the dilution water is at a temperature that is no greater than 20° C. less and preferably no greater than 10° C. less than the temperature of the mixture. In particularly preferred embodiments, the dilution water is at a temperature no greater than 5° C. less than that of the activation process mixture throughout the time that it is added.

For the avoidance of doubt, if the temperature of hot mixture is x° C., it is preferred that the temperature of the dilution water is at least x−20° C. and more preferred that it is at least x−10° C.

Herein, amounts and concentrations of ingredients are percentages by weight of the total composition, unless otherwise indicated and ratios are ratios by weight.

A preferred additional component of compositions manufactured according to the invention is an oil.

Herein, the terms "oil" and signifies a water-insoluble organic material that is liquid at 20° C. Any material having a solubility of less than 0.1 g/100 g at 20° C. is considered to be insoluble.

Herein "aqueous compositions" are compositions having a continuous phase that is predominately water; that is to say, greater than 50% water.

Other components may also be including in antiperspirant compositions manufactured according to the invention.

A preferred oil for use in accordance with the present invention is a fragrance oil, sometimes alternatively called a perfume oil. The fragrance oil may comprise a single fragrance or component more commonly a plurality of fragrance components. Herein, fragrance oils impart an odour, preferably a pleasant odour, to the composition. Preferably, the fragrance oil imparts a pleasant odour to the surface of the human body the composition is applied to the same.

The amount of fragrance oil in the composition is commonly up to 3% advantageously is at least 0.5% and particularly from 0.8% to 2%.

The total amount of oil in the composition is preferably from 0.1 to 20%, more preferably from 0.5 to 10%, and most preferably at from 2 to 8% by weight of the total composition. In certain preferred embodiments, particularly those also comprising an aluminium and/or zirconium containing antiperspirant active, the oil is present at greater than 2.5% and less than 6% by weight of the total composition.

In certain embodiments, it is preferred to include an oil, other than a fragrance oil, that has a relatively low viscosity, by which is meant less 250 cS (mm$^2 \cdot$s$^{-1}$). Such oils can improve the sensory properties of the composition on application and can lead to other benefits such as emolliency.

Suitable oils can be selected from alkyl ether oils having a boiling point of above 100° C. and especially above 150° C., including polyalkyleneglycol alkyl ethers. Such ethers desirably comprise between 10 and 20 ethylene glycol or propylene glycol units and the alkyl group commonly contains from 4 to 20 carbon atoms. The preferred ether oils include polypropylene glycol alkyl ethers such as PPG-14-butylether and PPG-15-stearyl ether.

Suitable oils can include one or more triglyceride oils. The triglyceride oils commonly comprise the alkyl residues of aliphatic $C_7$ to $C_{20}$ alcohols, the total number of carbon atoms being selected in conjunction with the extent of olefinic unsaturation and/or branching to enable the triglyceride to be liquid at 20° C. One example is jojoba oil. Particularly preferably, in the triglyceride oil the alkyl residues are linear $C_{18}$ groups having one, two or three olefinic degrees of unsaturation, two or three being optionally conjugated, many of which are extractable from plants (or their synthetic analogues), including triglycerides of oleic acid, linoleic acid, conjugated linoleic acids, linolenic acid, petroselenic acid, ricinoleic acid, linolenelaidic acid, trans 7-octadecenoic acid, parinaric acid, pinolenic acid, punicic acid, petroselenic acid and stearidonic acid.

Suitable oils can include those derived from unsaturated 018 acids, including coriander seed oil, impatiens balsimina seed oil, parinarium laurinarium kernel fat oil, sabastiana brasilinensis seed oil, dehydrated castor seed oil, borage seed oil, evening primrose oil, aquilegia vulgaris oil, sunflower (seed) oil and safflower oil. Other suitable oils are obtainable from hemp, and maize corn oil. An especially preferred oil by virtue of its characteristics is sunflower (seed) oil.

Further suitable oils, that can also be emollient oils, comprise alkyl or alkyl-aryl ester oils having a boiling point of above 150° C. (and a melting point of below 20° C.). Such ester oils include oils containing one or two alkyl groups of 12 to 24 carbon atoms length, including isopropyl myristate, isopropyl palmitate and myristyl palmitate. Other non-volatile ester oils include alkyl or aryl benzoates such 012-15 alkyl benzoate, for example Finsolv TN™ or Finsolv Sun™.

A further class of suitable oils comprises non-volatile dimethicones, often comprising phenyl or diphenylene substitution, for example Dow Corning 200 350 cps or Dow Corning 556.

A preferred component in many antiperspirant compositions, particularly aqueous antiperspirant compositions manufactured according to the invention is an emulsifier. Emulsifiers are particularly advantageous in aqueous systems additionally comprising fragrance oil and/or other oil.

Preferred compositions manufactured according to the invention are oil-in-water emulsions comprising an emulsifier, such compositions giving especially effective antiperspirancy, especially when the molar ratio of calcium to aluminium and/or amino acid to aluminium is within the preferred ranges indicated above (vide supra).

It is preferred that emulsifiers used in aqueous antiperspirant compositions manufactured according to the present invention form a lamellar phase emulsifier system in the composition. Such systems may be readily identified by means of optical microscopy. Such systems lead to good emulsion stability in compositions according to the invention.

It is preferred that aqueous antiperspirant compositions manufactured according to the present invention comprise a non-ionic emulsifier system. Such an emulsifier system conveniently has a mean HLB value in the region of from about 5 to about 12 and particularly from 6 to about 10. In the preferred embodiments referred to in the paragraph immediately above, an especially desired mean HLB value is from 6 to 9. Such a mean HLB value can be provided by selecting an emulsifier having such an HLB value, or more preferably by employing a combination of at least two emulsifiers, a first (lower) HLB emulsifier having an HLB value in the range of from 2 to 6.5, such as in particular from 4 to 6 and a second (higher) HLB emulsifier having an HLB value in the range of from about 6.5 to 18 and especially from about 12 to about 18. When a combination of emulsifiers is employed, the average HLB value can be calculated as a weight average of the HLB values of the constituent emulsifiers.

Lamellar phase emulsifier systems preferably comprise two non-ionic surfactants, optionally selected as suggested in the paragraph immediately above. In a particular embodiment a first emulsifier is a fatty alcohol, such as cetyl and/or stearyl alcohol and a second emulsifier is much more hydrophilic, having a HLB of from about 6.5 to 18 and especially from about 12 to about 18.

An especially desirable range of emulsifiers comprises a hydrophilic moiety provided by a polyalkylene oxide (polyglycol), and a hydrophobic moiety provided by an aliphatic hydrocarbon, preferably containing at least 10 carbons and commonly linear. The hydrophobic and hydrophilic moieties can be linked via an ester or ether linkage, possibly via an intermediate polyol such as glycerol. A preferred range of emulsifiers comprises polyethylene glycol ethers.

Preferably the hydrophobic aliphatic substituent contains at least 12 carbons, and is derivable from lauryl, palmityl, cetyl, stearyl, and behenyl alcohol, and especially cetyl, stearyl or a mixture of cetyl and stearyl alcohols or from the corresponding carboxylic acids.

The polyalkylene oxide is often selected from polyethylene oxide and polypropylene oxide or a copolymer of ethylene oxide and especially comprises a polyethylene oxide. The number of alkylene oxide and especially of ethoxylate units within suitable emulsifiers is often selected within the range of from 2 to 100. Emulsifiers with a mean number of ethoxylate units in the region of 2 can provide a lower HLB value of below 6.5 and those having at least 4 such units provide a higher HLB value of above 6.5 and especially those containing at least 10 ethoxylate units which provide an HLB value of above 10. A preferred combination comprises a mixture of an ethoxylate containing 2 units and one containing from 10 to 40 units, such as from 15 to 30 or desirably from 20 to 25. Particularly conveniently, the combination of emulsifiers comprises steareth-2 and a selection from steareth-15 to steareth-30.

It is desirable to employ a mixture of ethoxylated alcohol emulsifiers in a weight ratio of emulsifier having a lower HLB value of less than 6.5 to emulsifier having a higher HLB value of greater than 8 of from 2:1 to 6:1 and particularly from 4:1 to 6:1.

The total proportion of emulsifiers in the composition is usually at least 1% and particularly at least 2% by weight. Commonly, the emulsifiers are not present at above 10%, often not more than 7% by weight and in many preferred embodiments up to 6% by weight. An especially desirable concentration range for the emulsifiers is from 2.5 to 5% by weight.

Other components that may be present include short chain ($C_2$-$C_4$) alcohols and especially polyols such glycerol, ethylene glycol, propylene glycol and polymers thereof, in particular poly(ethylene glycol) and poly(propylene glycol). Poly(ethylene glycol) of average molecular weight 200 to 600 is a preferred component. Such components may add to the sensory properties of the composition and, when included, are typically present at from 0.5 to 10% of the total composition.

The aqueous compositions manufactured according to the present invention are very suitable for dispensing via a roll-on dispenser, for example any upright dispenser such as described in EP1175165 or an invert dispenser such as described in U.S. Pat. No. 6,511,243 or WO05/007377. Invert indicates that the dispenser stands stably with its dispensing ball below the formulation reservoir. In using such dispensers, the composition is applied by rolling the ball of the dispenser across the skin surface, depositing a film of fluid on the skin. Commonly the dispenser is wiped across the skin between 4 and 10 strokes. Commonly from 0.2 to 0.5 g of the composition is deposited in each armpit per application.

The method of attaining an antiperspirant benefit described as the third aspect of the invention (vide supra) may involve direct or indirect topical application to the composition surface of the human body.

EXAMPLES

Example 1

81.9 parts of an aqueous solution of ASCH (40% anhydrous solids), 5.27 parts calcium chloride dihydrate and 12.83 parts glycine were heated at 87° C. for 1 hour.

Samples of the above solution, having an anhydrous solids content of 49.57%, were then diluted with water to 24.26% anhydrous solids (i.e. by 2.04) using the following methods.

1.1 Whilst still at 87° C., a sample was diluted with water also at 87° C.
1.2 Whilst still at 87° C., a sample was diluted with water at 20° C.
1.3 Whilst still at 87° C., a sample was diluted with water at 35° C.
1.4 A further sample was cooled to 20° C. and then diluted with water also at 20° C.
1.5 A further sample was cooled to 35° C. and then diluted with water also at 35° C.
1.6 A further sample was cooled to 35° C. and then diluted with water at 20° C.

The diluted samples as described above were placed on storage at 20° C. and their viscosities monitored. The results observed are indicated in Table 1.

Viscosities were measured at 25° C. at a shear rate of 10 rpm over 1 minute using an Anton Paar MCR301 rheometer.

TABLE 1

| Sample | T1 (° C.) | T2 (° C.) | Viscosity (mPa · s) after . . . | | | |
|---|---|---|---|---|---|---|
| | | | 0 days | 6 days | 8 days | 10 days | 15 days |
| 1.1 | 87 | 87 | 2 | — | 2 | — | 3 |
| 1.2 | 87 | 20 | 2 | — | 22 | — | 105 |
| 1.3 | 87 | 35 | 2 | — | 15 | — | 100 |
| 1.4 | 20 | 20 | 4 | 55 | — | 190 | — |
| 1.5 | 35 | 35 | 4 | 96 | — | 200 | — |
| 1.6 | 35 | 20 | 3 | 93 | — | 202 | — |

0 day measurements were made within 1 hour of dilution.
T1 = mixture temperature before dilution.
T2 = temperature of water used for the dilution.

The results in Table indicate that viscosity stability is better for the samples not cooled before dilution, i.e. samples 1.1, 1.2, and 1.3. The results further indicate that sample 1.1, which was diluted whilst still hot and with hot water, had by far the best viscosity stability. Further storage of this sample revealed that its viscosity was still in single figures after 34 days.

Example 2

As in Example 1, 81.9 parts of an aqueous solution of ASCH (40% anhydrous solids), 5.27 parts calcium chloride dihydrate and 12.83 parts glycine were heated at 87° C. for 1 hour. This preparation was performed at a range of heating rates and cooling rates as described below.

2.1 Heated from 20° C. to 87° C. in 20 minutes (i.e. 3.35° C. per minute) and cooled back down to 25° C. in 45 minutes (i.e. 1.38° C. per minute).
2.2 Heated from 20° C. to 87° C. in 60 minutes (i.e. 1.12° C. per minute) and cooled back down to 25° C. in 45 minutes (i.e. 1.38° C. per minute).

2.3 Heated from 20° C. to 87° C. in 20 minutes (i.e. 3.35° C. per minute) and cooled back down to 25° C. in 240 minutes (i.e. 0.26° C. per minute).

2.4 Heated from 20° C. to 87° C. in 60 minutes (i.e. 1.12° C. per minute) and cooled back down to 25° C. in 240 minutes (i.e. 0.26° C. per minute).

The resulting solutions were placed on storage at 15° C. and their viscosities monitored. The results observed are indicated in Table 2. Viscosities were measured as for the results given in Table 1.

TABLE 2

| Sample | R1 (° C./min.) | R2 (° C./min.) | Viscosity (mPa · s) after . . . | | | | |
|---|---|---|---|---|---|---|---|
| | | | 0 days | 1 day | 2 days | 3 days | 4 days |
| 2.1 | 3.35 | 1.38 | 20.8 | 21.4 | 22.3 | 24.6 | 27.8 |
| 2.2 | 1.12 | 1.38 | 25.9 | 26.4 | 28.9 | 33.3 | 38.9 |
| 2.3 | 3.35 | 0.26 | 24.7 | 30.9 | 43.6 | 147 | 514 |
| 2.4 | 1.12 | 0.26 | 36.5 | 47.2 | 76.8 | 285 | 600 |

R1 = Heating rate.
R2 = Cooling rate.

These results indicate that solutions cooled at a rate of 1.49° C. per minute have far superior viscosity stability compared to those cooled at a rate of 0.28° C. per minute. This is turn means that the solutions cooled at the quicker rate do not need to be further diluted as quickly as those prepared at the slower rate. It is further observed that solutions cooled at the faster rate produce rheologically superior antiperspirant compositions following their dilution according to the invention.

It may also be noted the results in Table 2 that the rate of heating had relatively little impact upon the viscosity stability.

Example 3

30 parts of ASCH powder (Reach 301; 80% anhydrous solids), 3.0 parts anhydrous calcium chloride, 9.4 parts glycine and 57.6 parts water were heated at 85° C. for 18 hours. This resulted in a solution of an antiperspirant solution (AP3) having 36.4% anhydrous solids and a Band III content of 69%. Following cooling to ambient temperature and dilution with water in accordance with the invention, the antiperspirant composition detailed in Table 3 was arrived at by additional methods known in art.

TABLE 3

| Component: | % w/w |
|---|---|
| Antiperspirant solution AP3 | 50 |
| Water | 43.8 |
| Steareth 20 (1) | 0.9 |
| Steareth 2 (2) | 2.3 |
| Sunflower Seed Oil (3) | 2.0 |
| Fragrance | 1.0 |

The invention claimed is:

1. A process for manufacture of an antiperspirant composition comprising the reaction of an aqueous solution of aluminium sesquichlorohydrate, water soluble calcium salt and amino acid, at a total anhydrous solids content of from 33 to 60% by weight and at a temperature of at least 65° C., for a period of from 1 to 24 hours, wherein the molar ratio of water soluble calcium salt to aluminium sesquichlorohydrate is at least 1:40 and the molar ratio of amino acid to aluminium sesquichlorohydrate is at least 1:20, the mixture then being subjected to a cooling phase in which it is cooled to less than 25° C. and a dilution phase in which it is diluted to a total anhydrous solids content of less than 25% by weight, the dilution phase being performed within 10 days of cooling phase.

2. The process according to claim 1, wherein the aluminium sesquichlorohydrate is of formula $Al_2(OH)_{4.4}Cl_{1.6}$ to $Al_2(OH)_{4.9}Cl_{1.1}$.

3. The process according to claim 1, wherein the molar ratio of water soluble calcium salt to aluminium sesquichlorohydrate is at least 1:20 and the molar ratio of amino acid to aluminium sesquichlorohydrate is at least 1:10.

4. The process according to claim 1, the reaction of the aqueous solution of aluminium sesquichlorohydrate, water soluble calcium salt and amino acid is continued until a Band III content of at least 40% is achieved.

5. The process according to claim 1, wherein in the cooling phase the mixture is cooled to less than 25° C. at a rate of at least 0.9° C. per minute.

6. The process according to claim 1, wherein the mixture is still at a temperature of at least 65° C. when the dilution phase is commenced.

7. The process according to claim 6, wherein the temperature of the water used for the dilution is no greater than 20° C. less than the temperature of the mixture to which it is added.

8. The process according to claim 7, wherein the temperature of the water used for the dilution is no greater than 10° C. less than the temperature of the mixture to which it is added.

9. The process according to claim 1, wherein the dilution phase is performed within 5 days of the cooling phase.

10. The process according to claim 1, wherein the activation process is performed at an anhydrous solids level of at least 40% by weight.

11. The process according to claim 1, wherein the dilution is carried out within 7 days of the cooling phase.

12. An aqueous antiperspirant composition prepared according to claim 1.

13. An aqueous antiperspirant composition prepared according to claim 10.

14. A cosmetic method of attaining an antiperspirancy benefit comprising the topical application of a composition according to claim 11 the surface of the human body.

15. The process according to claim 1 wherein the aluminium sesquichlorohydrate is of formula $Al_2(OH)_{4.7}Cl_{1.3}$ to $Al_2(OH)_{4.9}Cl_{1.1}$.

16. The process according to claim 1 wherein the reaction of the aqueous solution of aluminium sesquichlorohydrate, water soluble calcium salt and amino acid is continued until a Band III content of at least 50% is achieved.

17. The process according to claim 1 wherein the reaction of the aqueous solution of aluminium sesquichlorohydrate, water soluble calcium salt and amino acid is continued until a Band III content of at least 60% is achieved.

* * * * *